(12) United States Patent
Gan

(10) Patent No.: US 6,645,670 B2
(45) Date of Patent: Nov. 11, 2003

(54) EFFICIENT CELL STACK FOR CELLS WITH DOUBLE CURRENT COLLECTORS SANDWICH CATHODES

(75) Inventor: Hong Gan, East Amherst, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 208 days.

(21) Appl. No.: 09/845,875

(22) Filed: Apr. 30, 2001

(65) Prior Publication Data

US 2001/0049032 A1 Dec. 6, 2001

Related U.S. Application Data

(60) Provisional application No. 60/204,477, filed on May 16, 2000.

(51) Int. Cl.⁷ ............................................... H01M 4/02
(52) U.S. Cl. ............... 429/209; 429/231.7; 429/219; 429/220; 429/221; 429/224; 429/231.5; 429/231.1; 429/233; 429/245; 429/330; 429/333; 429/335; 429/322; 429/323; 29/623.1
(58) Field of Search ................ 429/209, 231.7, 429/219, 221, 220, 224, 231.5, 231.1, 233, 245, 330, 333, 335, 322, 323; 29/623.1

(56) References Cited

U.S. PATENT DOCUMENTS

| | | | |
|---|---|---|---|
| 2,594,712 A | 4/1952 | Andre | 136/6 |
| 2,661,388 A | 12/1953 | Warner et al. | 136/100 |
| 2,662,928 A | 12/1953 | Brennan | 136/24 |
| 2,669,594 A | 2/1954 | Andre | 136/6 |
| 3,736,184 A | 5/1973 | Dey et al. | |
| 4,091,185 A | 5/1978 | Chireau et al. | 429/144 |
| 4,098,967 A | 7/1978 | Biddick et al. | 429/210 |
| 4,211,833 A | 7/1980 | Einstein | 429/149 |
| 4,960,655 A | 10/1990 | Hope et al. | 429/192 |
| 5,180,642 A | * 1/1993 | Weiss et al. | 429/231.5 |
| 5,322,746 A | 6/1994 | Wainwright | 429/60 |
| 5,368,952 A | 11/1994 | Sonneveld | 429/67 |
| 5,368,961 A | 11/1994 | Juergens | 429/233 |
| 5,478,668 A | 12/1995 | Gozdz et al. | 429/127 |
| 5,658,694 A | 8/1997 | Charkey | 429/229 |
| 5,667,916 A | * 9/1997 | Ebel et al. | 429/219 |
| 5,744,258 A | 4/1998 | Bai et al. | |
| 5,811,206 A | * 9/1998 | Sunderland et al. | 429/181 |
| 5,894,656 A | 4/1999 | Menon et al. | 29/623.1 |
| 5,955,217 A | 9/1999 | Van Lerberghe | 429/162 |
| 5,993,999 A | 11/1999 | Rivers et al. | 429/244 |
| 6,051,333 A | 4/2000 | Nagai et al. | 429/94 |

FOREIGN PATENT DOCUMENTS

| | | |
|---|---|---|
| EP | 0 532 313 A1 | 3/1993 |
| EP | 0 689 256 A1 | 12/1995 |

* cited by examiner

Primary Examiner—Laura Weiner
(74) Attorney, Agent, or Firm—Michael F. Scalise

(57) ABSTRACT

The present invention improves the performance of lithium electrochemical cells by providing a new electrode assembly based on a sandwich cathode design, but termed a double screen sandwich cathode electrode design. In particular, the present invention uses sandwich cathode electrodes which are, in turn, sandwiched between two half double screen sandwich cathode electrodes, either in a prismatic plate or serpentine-like electrode assembly. In a jellyroll electrode assembly, the cell is provided in a case-positive design and the outside round of the electrode assembly is a half double screen sandwich cathode electrode.

30 Claims, 3 Drawing Sheets

EFFICIENT CELL STACK FOR CELLS WITH DOUBLE CURRENT COLLECTORS SANDWICH CATHODES

CROSS REFERENCE TO RELATED APPLICATION

The present invention claims priority based on provisional application Serial No. 60/204,477, filed May 16, 2000.

BACKGROUND OF THE INVENTION

1. Field of the Invention

The present invention relates to the conversion of chemical energy to electrical energy. More particularly, this invention relates to a design for a defibrillator cell, such as a prismatic cell stack, containing double screen sandwich cathodes. Double screen sandwich cathode electrodes are based on a novel cathode configuration termed a sandwich cathode electrode. The structure of a sandwich cathode electrode will be described in detail hereinafter as well as how it differs from a double screen sandwich cathode electrode of the present invention.

2. Prior Art

Implantable ventricular cardiac defibrillators typically use lithium/silver vanadium oxide (Li/SVO) electrochemical cells as their power source. For the implantable medical device itself, it is preferable that the device be relatively small in size, quick in response to the patient's medical needs, promote long device service life, etc. Therefore, when cells are built for implantable medical applications, special electrode assembly designs are needed to meet all of these requirements. Additionally, for cells powering cardiac defibrillators, a large electrode surface area is required to provide the needed power capability. An efficient cell package is also needed to achieve the highest capacity in the smallest volume.

In a conventional electrode assembly for Li/SVO cells, the cathode active material is pressed, coated or otherwise contacted to both sides of a foil or screen cathode current collector to provide the cathode electrode. Lithium as the anode active material in the form of a foil is pressed onto both sides of an anode current collector to form the anode electrode. The anode and the cathode electrodes are then placed against each other with one or two layers of intermediate separator material. The final electrode assembly is typically in the form of a prismatic plate design or a jellyroll design. An example of the conventional prismatic plate design is disclosed in U.S. Pat. No. 5,147,737 to Post et al. An example of a conventional jellyroll design is disclosed in U.S. Pat. No. 5,439,760 to Howard et al.

To further illustrate this point, FIG. 1 shows a detailed cross-sectional view of the electrode assembly 10 of either a conventional prismatic plate design or a conventional jellyroll design. The electrode assembly 10 comprises an anode electrode 12 and a cathode electrode 14 physically segregated from each other by separator sheets 16. The anode electrode 12 comprises an anode active material 18, such as lithium, contacted to at least one side of an anode current collector 20. Similarly, the cathode electrode 14 comprises a cathode active material 22, such as SVO or $CF_x$, contacted to at least one side of a cathode current collector 24. Whether the cell is of a prismatic plate or jellyroll configuration, they are typically built in a case-negative configuration with the anode current collector 20 having an outermost position in contact with the casing (not shown) as the anode or negative terminal. The cathode electrode is contacted to a terminal lead (not shown) insulated from the casing by a glass-to-metal seal, as is well known by those skilled in the art.

Depending on the number of plates in the prismatic configuration, or the number of winds in a jellyroll cell, the conventional electrode assembly 10 can have n repeating units of the anode electrode 12 and the cathode electrode 14. This is shown in FIG. 1 where n=0, 1, 2, 3, 4, 5, etc.

U.S. patent application Ser. No. 09/560,060, filed Apr. 27, 2000, which is assigned to the assignee of the present invention and incorporated herein by reference, describes a sandwich cathode electrode design for defibrillator applications. The sandwich cathode electrode design is believed to be a pioneering improvement over the conventional prismatic and jellyroll electrode assemblies. In the sandwich cathode electrode design, the cathode electrode is prepared using two distinct and different cathode active materials and two cathode current collectors. The first cathode active material is sandwiched between the two current collectors and this assembly is, in turn, sandwiched between two layers of the second cathode active material.

A cross-sectional view of a sandwich cathode electrode assembly is presented in FIG. 2. This figure shows an electrode assembly 30 including an anode electrode 32 and a cathode electrode 34 segregated from each other by separator sheets 36. The anode electrode comprises an anode active material 38, such as lithium, contacted to at least one side of an anode current collector 40, such as of nickel. In that respect, the anode electrode 32 of the electrode assembly 30 is the same as the anode electrode described with respect to FIG. 1.

The electrode assembly 30 further includes the sandwich cathode electrode 34 having spaced apart cathode current collectors 42 and 44 with a first cathode active material 46 sandwiched between them. The cathode active material 46 is of a relatively high energy density but of a relatively low rate capability. A second cathode active material 48, different than that of the first cathode active material 46, is contacted to the opposite sides of the current collectors 42, 44. The second cathode active material is of a relatively low energy density but of a relatively high rate capability. This electrode assembly is the fundamental structure for an electrochemical cell having a sandwich cathode electrode. As with the electrode assembly shown in FIG. 1, the electrode assembly 30 is typically built in a case-negative design.

Since the sandwich cathode electrode design is completely different from conventional prismatic and jellyroll cathode electrode designs, the most efficient electrode assembly for conventional cells is not the most efficient assembly for cells with sandwich cathode electrodes. For this reason, the present invention discloses a new efficient cell stack design utilizing sandwich cathode electrodes in combination with half double screen sandwich cathode electrodes as the cell stack components. This new electrode assembly based on the sandwich cathode electrode design is termed a double screen sandwich cathode electrode design.

SUMMARY OF THE INVENTION

The present invention improves the performance of lithium electrochemical cells by providing a new electrode assembly based on a sandwich cathode design. The present invention is termed a double screen sandwich cathode electrode design. Cells powering implantable medical devices, such as a cardiac defibrillator, and utilizing a double screen sandwich cathode electrode have improved volumetric efficiency. In particular, the present invention uses sandwich cathode electrodes which are, in turn, sandwiched between two half double screen sandwich cathode electrodes, either in a prismatic plate or serpentine-like electrode assembly. In a jellyroll electrode assembly, the cell is provided in a case-positive design and the outside round of the electrode assembly is a half double screen sandwich cathode electrode.

These and other objects of the present invention will become increasingly more apparent to those skilled in the art by reference to the following description.

DETAILED DESCRIPTION OF THE PREFERRED EMBODIMENTS

Figure 1:
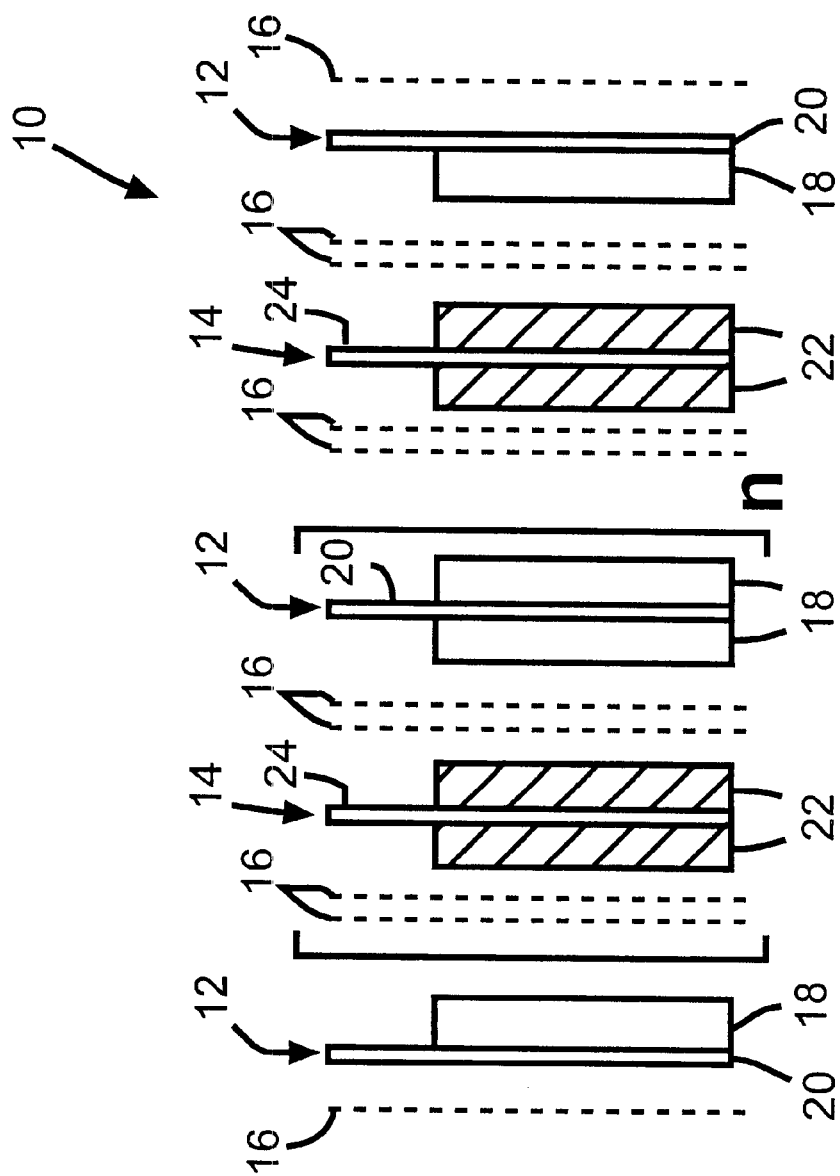
FIG. 1 is a cross-sectional view of an electrochemical cell including either a prismatic plate or a jellyroll electrode assembly according to the prior art.

An electrochemical cell that possesses a double screen sandwich cathode electrode design according to the present invention must have sufficient energy density and discharge capacity in order to be a suitable power source for implantable medical devices. Such cells comprise an anode of a metal selected from Groups IA, IIA and IIIB of the Periodic Table of the Elements. These anode active materials include lithium, sodium, potassium, etc., and their alloys and intermetallic compounds including, for example, Li—Si, Li—Al, Li—B and Li—Si—B alloys and intermetallic compounds. The preferred anode comprises lithium. An alternate anode comprises a lithium alloy such as a lithium-aluminum alloy. The greater the amount of aluminum present by weight in the alloy, however, the lower the energy density of the cell.

The form of the anode may vary, but preferably the anode is a thin metal sheet or foil of the anode metal, pressed or rolled on a metallic anode current collector, i.e., preferably comprising titanium, titanium alloy or nickel, to form an anode component. Copper, tungsten and tantalum are also suitable materials for the anode current collector. In the exemplary cell of the present invention, the anode component has an extended tab or lead of the same material as the anode current collector, i.e., preferably nickel or titanium, integrally formed therewith such as by welding and contacted by a weld to a cell case of conductive metal in a case-negative electrical configuration. Alternatively, the anode may be formed in some other geometry, such as a bobbin shape, cylinder or pellet to allow an alternate low surface cell design.

The electrochemical cell of the present invention further comprises a cathode of electrically conductive material which serves as the other electrode of the cell. The cathode is preferably of solid materials and the electrochemical reaction at the cathode involves conversion of ions which migrate from the anode to the cathode into atomic or molecular forms. The solid cathode may comprise a first active material of a metal element, a metal oxide, a mixed metal oxide and a metal sulfide, and combinations thereof and a second active material of a carbonaceous chemistry. The metal oxide, the mixed metal oxide and the metal sulfide of the first active material have a relatively lower energy density but a relatively higher rate capability than the second active material.

The first active material is formed by the chemical addition, reaction, or otherwise intimate contact of various metal oxides, metal sulfides and/or metal elements, preferably during thermal treatment, sol-gel formation, chemical vapor deposition or hydrothermal synthesis in mixed states. The active materials thereby produced contain metals, oxides and sulfides of Groups, IB, IIB, IIIB, IVB, VB, VIB, VIIB and VIII, which includes the noble metals and/or other oxide and sulfide compounds. A preferred cathode active material is a reaction product of at least silver and vanadium.

One preferred mixed metal oxide is a transition metal oxide having the general formula $SM_xV_2O_y$ where SM is a metal selected from Groups IB to VIIB and VIII of the Periodic Table of Elements, wherein x is about 0.30 to 2.0 and y is about 4.5 to 6.0 in the general formula. By way of illustration, and in no way intended to be limiting, one exemplary cathode active material comprises silver vanadium oxide having the general formula $Ag_xV_2O_y$ in any one of its many phases, i.e., β-phase silver vanadium oxide having in the general formula x=0.35 and y=5.8, γ-phase silver vanadium oxide having in the general formula x=0.80 and y=5.40 and ε-phase silver vanadium oxide having in the general formula x=1.0 and y=5.5, and combinations and mixtures of phases thereof. For a more detailed description of such cathode active materials reference is made to U.S. Pat. No. 4,310,609 to Liang et al., which is assigned to the assignee of the present invention and incorporated herein by reference.

Another preferred composite transition metal oxide cathode active material is copper silver vanadium oxide (CSVO) having the general formula $Cu_xAg_yV_2O_z$. This active material includes $V_2O_z$ wherein $z \leq 5$ combined with $Ag_2O$ with silver in either the silver(II), silver(I) or silver(0) oxidation state and CuO with copper in either the copper(II), copper(I) or copper(0) oxidation state. Thus, the composite cathode active material may be described as a metal oxide-metal oxide-metal oxide, a metal-metal oxide-metal oxide, or a metal-metal-metal oxide and the range of material compositions found for $Cu_xAg_yV_2O_z$ is preferably about $0.01 \leq z \leq 6.5$. Typical forms of CSVO are $Cu_{0.16}Ag_{0.67}V_2O_z$ with z being about 5.5 and $Cu_{0.5}Ag_{0.5}V_2O_z$ with z being about 5.75. The oxygen content is designated by z since the exact stoichiometric proportion of oxygen in CSVO can vary depending on whether the cathode material is prepared in an oxidizing atmosphere such as air or oxygen, or in an inert atmosphere such as argon, nitrogen and helium. For a more detailed description of this cathode active material reference is made to U.S. Pat. No. 5,472,810 to Takeuchi et al. and U.S. Pat. No. 5,516,340 to Takeuchi et al., both of which are assigned to the assignee of the present invention and incorporated herein by reference.

The sandwich cathode design of the present invention further includes a second active material of a relatively high energy density and a relatively low rate capability in comparison to the first cathode active material. The second active material is preferably a carbonaceous compound prepared from carbon and fluorine, which includes graphitic and nongraphitic forms of carbon, such as coke, charcoal or activated carbon. Fluorinated carbon is represented by the formula $(CF_x)_n$ wherein x varies between about 0.1 to 1.9 and preferably between about 0.5 and 1.2, and $(C_2F)_n$ wherein the n refers to the number of monomer units which can vary widely.

In a broader sense, it is contemplated by the scope of the present invention that the first cathode active material is any material which has a relatively lower energy density but a relatively higher rate capability than the second cathode active material. In addition to silver vanadium oxide and copper silver vanadium oxide, $V_2O_5$, $MnO_2$, $LiCoO_2$, $LiNiO_2$, $LiMn_2O_4$, $TiS_2$, $Cu_2S$, FeS, $FeS_2$, copper oxide, copper vanadium oxide, and mixtures thereof are useful as the first active material, and in addition to fluorinated carbon, $Ag_2O$, $Ag_2O_2$, $CuF_2$, $Ag_2CrO_4$, $MnO_2$ and even SVO itself are useful as the second active material.

Before fabrication into a double screen sandwich electrode for incorporation into an electrochemical cell according to the present invention, the first and second cathode active materials prepared as described above are preferably mixed with a binder material such as a powdered fluoropolymer, more preferably powdered polytetrafluoroethylene or powdered polyvinylidene flouride present at about 1 to about 5 weight percent of the cathode mixture. Further, up to about 10 weight percent of a conductive diluent is preferably added to the cathode mixture to improve conductivity. Suitable materials for this purpose include acetylene black, carbon black and/or graphite or a metallic powder such as powdered nickel, aluminum, titanium and stainless steel. The preferred cathode active mixture thus includes a powdered fluoro-polymer binder present at about 3 weight percent, a conductive diluent present at about 3 weight percent and about 94 weight percent of the cathode active material.

Cathode components for incorporation into an electrochemical cell according to the present invention may be prepared by rolling, spreading or pressing the first and second cathode active materials onto a suitable current collector selected from the group consisting of stainless steel, titanium, tantalum, platinum, gold, aluminum, cobalt nickel alloys, nickel-containing alloys, highly alloyed ferritic stainless steel containing molybdenum and chromium, and nickel-, chromium- and molybdenum-containing alloys. The preferred current collector material is titanium, and most preferably the titanium cathode current collector has a thin layer of graphite/carbon material, iridium, iridium oxide or platinum applied thereto. Cathodes prepared as described above may be in the form of one or more plates operatively associated with at least one or more plates of anode material, or in the form of a strip wound with a corresponding strip of anode material in a structure similar to a "jellyroll".

In order to prevent internal short circuit conditions, the sandwich cathode is separated from the Group IA, IIA or IIIB anode by a suitable separator material. The separator is of electrically insulative material, and the separator material also is chemically unreactive with the anode and cathode active materials and both chemically unreactive with and insoluble in the electrolyte. In addition, the separator material has a degree of porosity sufficient to allow flow there through of the electrolyte during the electrochemical reaction of the cell. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric microporous film, non-woven glass, polypropylene, polyethylene, glass fiber materials, ceramics, a polytetrafluoroethylene membrane commercially available under the designation ZITEX (Chemplast Inc.), a polypropylene membrane commercially available under the designation CELGARD (Celanese Plastic Company, Inc.) and a membrane commercially available under the designation DEXIGLAS (C.H. Dexter, Div., Dexter Corp.).

Figure 2:
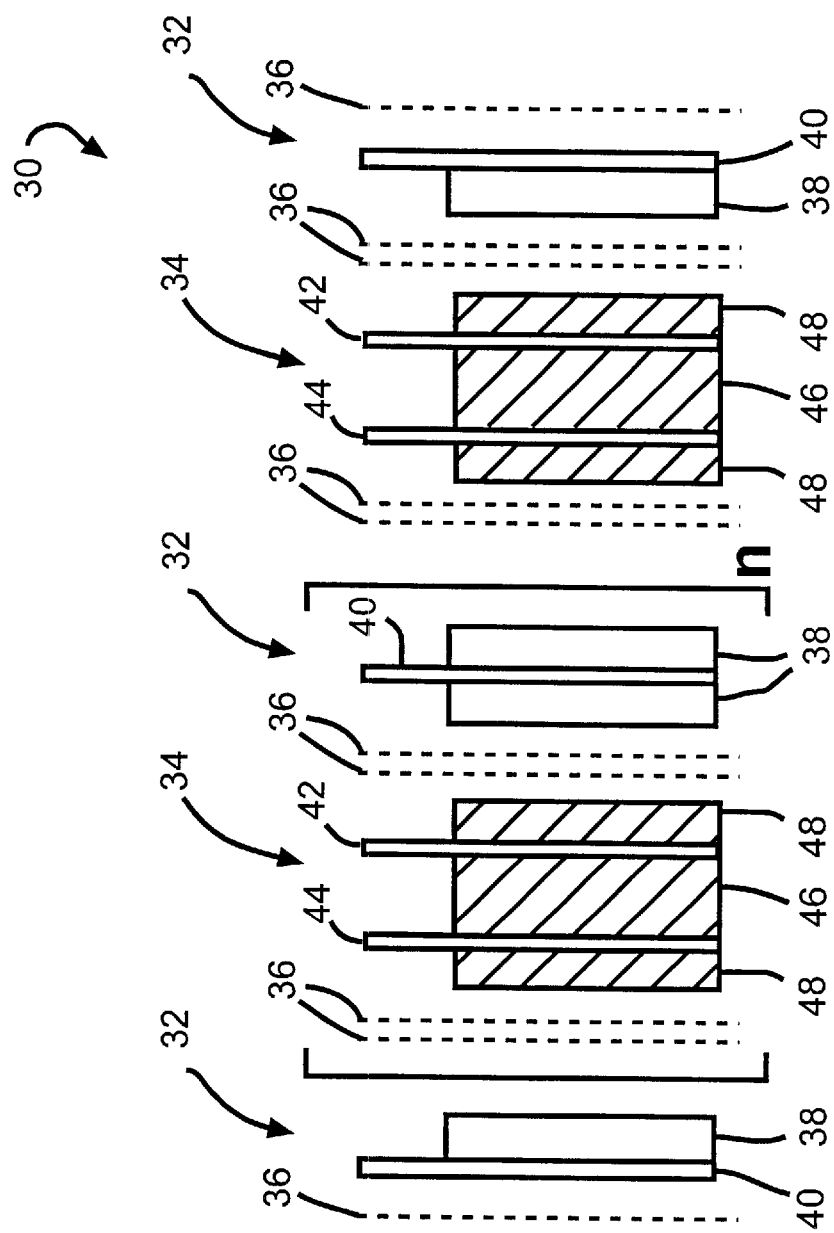
FIG. 2 is a cross-sectional view of an electrochemical cell including a sandwich cathode electrode design.
Figure 3:
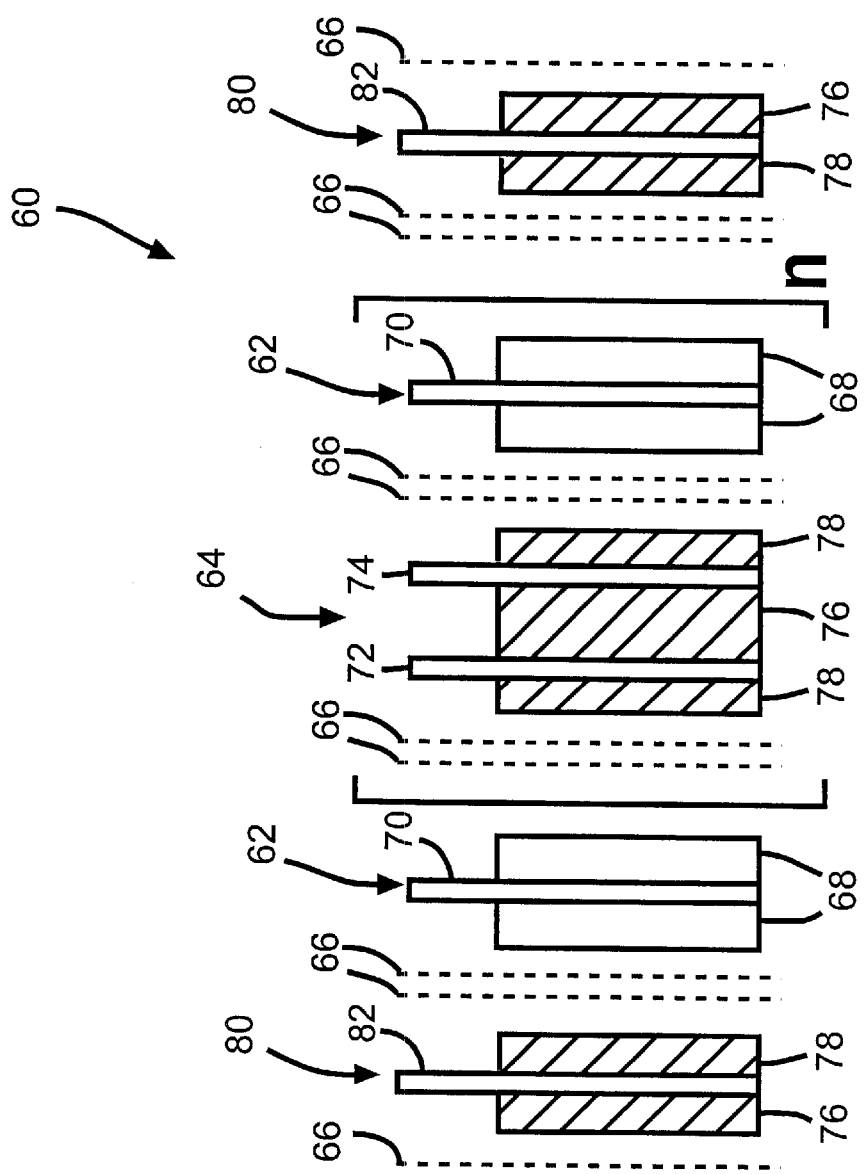
FIG. 3 is a cross-sectional view of an electrochemical cell including a double screen sandwich cathode electrode design according to the present invention.

FIG. 3 shows a detailed cross-sectional view of a double screen sandwich cathode electrode assembly 60 including an anode electrode 62 and a sandwich cathode electrode 64 segregated from each other by separator sheets 66. The anode electrode 62 comprises an anode active material 68, such as lithium, contacted to at least one side of an anode current collector 70. The sandwich cathode electrode 64 is the same as the sandwich cathode electrode 34 shown in FIG. 2 and includes spaced apart cathode current collectors 72 and 74 having a first cathode active material 76 sandwiched between them. As with the electrode of FIG. 2, the cathode active material 76 is of relatively high energy density but of a relatively low rate capability. A second cathode active material 78, different than that of the first cathode active material 76, is contacted to the opposite sides of the current collectors 72, 74. The second cathode active material 78 is of a relatively low energy density but of a relatively high rate capability.

Therefore, one exemplary sandwich cathode electrode design has the following configuration:

SVO/current collector/$CF_x$/current collector/SVO

Another sandwich cathode electrode design has the following configuration:

SVO/current collector/SVO/$CF_x$/SVO/current collector/SVO

The double screen sandwich cathode electrode assembly 60 further includes at least one half double screen sandwich cathode 80. The cathode 80 comprises a cathode current collector 82 having a third cathode active material 76 contacted to one side thereof, and a fourth cathode active material 78 contacted to the other side of the current collector. Preferably, the third cathode active material 76 is of a relatively high energy density but of a relatively low rate capability while the fourth cathode active material 78 is of a relatively low energy density but of a relatively high rate capability. The fourth cathode active material 78 faces the anode active material 68. Preferably, the first and third cathode active materials are the same and the second and fourth cathode active materials are the same.

An important aspect of the present invention is that the high capacity material having the low rate capability is preferably positioned between two layers of high rate cathode material (either high or low capacities). In other words, the exemplary $CF_x$ material never directly faces the lithium anode. In addition, the low rate cathode material must be short circuited with the high rate material, either by direct contact as demonstrated above in the second illustrated configuration, or by parallel connection through the current collectors as in the first illustrated configuration above.

The sandwich cathode electrode assembly illustrated in the previously described FIG. 2 has the following configuration:

SVO/screen/$CF_x$/screen/SVO

Depending on the number of plates in the cell, the electrode assembly 30 can have n repeating units of the anode electrode 32 and the cathode electrode 34. As shown in FIG. 2, n=0, 1, 2, 3, 4, 5, etc. In this cell stack design, the number of layers for each components is calculated as:

no. of separator layers=2(2n+3)

no. of lithium foil layers=2(n+1)

no. of anode screens=n+2 no. of SVO layers=2(n+1)

no. of $CF_x$ layers=n+1 no. of cathode screens=2(n+1)

Assuming n=1 in FIG. 2, there are ten separator layers, four lithium foil layers, three anode current collector screens, four SVO layers, two $CF_x$ layers and four current collector cathode screens.

A half double screen sandwich cathode is defined as SVO/screen/CF$_x$. In other words, the half double screen sandwich cathode can be thought of as having been provided by cutting a full sandwich cathode electrode in half down the middle of the CF$_x$ layer. The detailed cross section of a half double screen sandwich cathode is shown in the previously described FIG. 3. In this cell stack design, the number of layers for each components is calculated as:

no. of separator layers=2(2n+3)

no. of lithium foil layers=2(n+1)

no. of anode screens=n+1 no. of SVO layers=2(n+1)

no. of CF$_x$ layers=n+1 no. of cathode screens=2(n+1)

Assuming n=1 in FIG. 3, there are ten separator layers, four lithium foil layers, two anode current collector screens, four SVO layers, two CF$_x$ layers and four cathode current collector screens. Thus, it is apparent that in a comparison of the sandwich cathode electrode design shown in FIG. 2 with the double screen sandwich cathode electrode assembly show in FIG. 3, there is one less layer of anode current collector screen in the electrode assembly of the present invention. Since the electrode assembly thickness is the sum of the thickness of each component, the fewer the non-active component layers, the more volume for the active components and, consequently, the higher the cell's volumetric capacity. Therefore, the double screen sandwich cathode electrode assembly represents an improvement in cell packaging efficiency over that known before. The volumetric energy density of cells having an electrode assembly according to FIG. 3 of the present invention is higher than that of cells having a sandwich cathode electrode assembly, as shown in FIG. 2.

The electrochemical cell of the present invention further includes a nonaqueous, ionically conductive electrolyte which serves as a medium for migration of ions between the anode and the cathode electrodes during electrochemical reactions of the cell. The electrochemical reaction at the electrodes involves conversion of ions in atomic or molecular forms which migrate from the anode to the cathode. Thus, nonaqueous electrolytes suitable for the present invention are substantially inert to the anode and cathode materials, and they exhibit those physical properties necessary for ionic transport, namely, low viscosity, low surface tension and wettability.

A suitable electrolyte has an inorganic, tonically conductive salt dissolved in a nonaqueous solvent, and more preferably, the electrolyte includes an ionizable alkali metal salt dissolved in a mixture of aprotic organic solvents comprising a low viscosity solvent and a high permittivity solvent. The inorganic, tonically conductive salt serves as the vehicle for migration of the anode ions to intercalate or react with the cathode active materials. Preferably, the ion forming alkali metal salt is similar to the alkali metal comprising the anode.

In the case of an anode comprising lithium, the alkali metal salt of the electrolyte is a lithium based salt. Known lithium salts that are useful as a vehicle for transport of alkali metal ions from the anode to the cathode include LiPF$_6$, LiBF$_4$, LiAsF$_6$, LiSbF$_6$, LiClO$_4$, LiO$_2$, LiAlCl$_4$, LiGaCl$_4$, LiC(SO$_2$CF$_3$)$_3$, LiN (SO$_2$CF$_3$)$_2$, LiSCN, LiO$_3$SCF$_3$, LiC$_6$F$_5$SO$_3$, LiO$_2$CCF$_3$, LiSO$_6$F, LiB(C$_6$H$_5$)$_4$, LiCF$_3$SO$_3$, and mixtures thereof.

Low viscosity solvents useful with the present invention include esters, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy,2-methoxyethane (EME), ethyl methyl carbonate, methyl propyl carbonate, ethyl propyl carbonate, diethyl carbonate, dipropyl carbonate, and mixtures thereof, and high permittivity solvents including cyclic carbonates, cyclic esters, cyclic amides and a sulfoxide such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL), N-methyl-pyrrolidinone (NMP) and mixtures thereof. In the present invention, the preferred anode active material is lithium metal and the preferred electrolyte is 0.8M to 1.5M LiAsF$_6$ or LiPF$_6$ dissolved in a 50:50 mixture, by volume, of propylene carbonate as the preferred high permittivity solvent and 1,2-dimethoxyethane as the preferred low viscosity solvent.

It is appreciated that various modifications to the inventive concepts described herein may be apparent to those of ordinary skill in the art without departing from the spirit and scope of the present invention as defined by the appended claims.

What is claimed is:

1. An electrochemical cell, which comprises:

a) a first cathode structure of a first cathode active material of a first energy density and a first rate capability sandwiched between first and second cathode current collectors, and a second cathode active material of a second energy density and a second rate capability contacted to the first and second cathode current collectors opposite the first cathode active material, wherein the first energy density of the first cathode active material is greater than the second energy density while the first rate capability is less than the second rate capability of the second cathode active material;

b) a first anode structure of an alkali metal contacted to opposite sides of a first anode current collector, wherein the first anode structure is in electrical association with the second cathode active material contacting the first cathode current collector;

c) a second cathode structure having a third cathode active material of a third energy density and a third rate capability contacted to one side of a third cathode current collector, and a fourth cathode active material of a fourth energy density and a fourth rate capability contacted to the other side of the third cathode current collector, wherein the third energy density of the third cathode active material is greater than the fourth energy density while the third rate capability is less than the fourth rate capability of the fourth cathode active material and wherein the fourth cathode active material is in electrical association with the first anode structure opposite the second cathode active material contacting the first cathode current collector; and d) a nonaqueous electrolyte activating the first anode structure and the first and second cathode structures.

2. The electrochemical cell of claim 1 wherein the first and third cathode active materials are selected from the group consisting of CF$_x$, Ag$_2$O, Ag$_2$O$_2$, CuF, Ag$_2$CrO$_4$, MnO$_2$, silver vanadium oxide, and mixtures thereof, and wherein MnO$_2$ and silver vanadium oxide are only one of the first and third cathode active materials when the second and fourth cathode active materials are not MnO$_2$ or silver vanadium oxide and are of a lesser energy density and a greater rate capability than MnO$_2$ or silver vanadium oxide.

3. The electrochemical cell of claim 1 wherein the second and fourth cathode active materials are selected from the group consisting of silver vanadium oxide, copper silver vanadium oxide, $V_2O_5$, $MnO_2$, $LiCoO_2$, $LiNiO_2$, $LiMnO_2$, CuO, TiS, CuS, FeS, $FeS_2$, copper oxide, copper vanadium oxide, and mixtures thereof.

4. The electrochemical cell of claim 1 wherein the first and third cathode active materials are $CF_x$ and the second and fourth cathode active materials are silver vanadium oxide.

5. The electrochemical cell of claim 1 wherein the first cathode structure has the configuration: silver vanadium oxide/first cathode current collector/$CF_x$/second cathode current collector/silver vanadium oxide.

6. The electrochemical cell of claim 1 wherein the second cathode structure has the configuration: $CF_x$/third cathode current collector/silver vanadium oxide.

7. The electrochemical cell of claim 1 further including a second anode structure of the alkali metal contacted to opposite sides of a second anode current collector, wherein the second anode structure is in electrical association with the second cathode active material contacting the second cathode current collector.

8. The electrochemical cell of claim 7 further including a third cathode structure of a fifth cathode active material of a fifth energy density and a fifth rate capability contacted to one side of a fourth cathode current collector, and a sixth cathode active material of a sixth energy density and a sixth rate capability contacted to the other side of the fourth cathode current collector, wherein the fifth energy density of the fifth cathode active material is greater than the sixth energy density while the fifth rate capability is less than the sixth rate capability of the sixth cathode active material and wherein the sixth cathode active material is in electrical association with the second anode structure opposite the second cathode active material contacting the second cathode current collector.

9. The electrochemical cell of claim 8 wherein the first, third and fifth cathode active materials are selected from the group consisting of $CF_x$, $Ag_2O$, $Ag_2O_2$, CuF, $Ag_2CrO_4$, $MnO_2$, silver vanadium oxide, and mixtures thereof, and wherein $MnO_2$ and silver vanadium oxide are only one of the first and third cathode active materials when the second and fourth cathode active materials are not $MnO_2$ or silver vanadium oxide and are of are of a lesser energy density and a greater rate capability than $MnO_2$ or silver vanadium oxide.

10. The electrochemical cell of claim 8 wherein the second, fourth and sixth cathode active materials are selected from the group consisting of silver vanadium oxide, copper silver vanadium oxide, $V_2O_5$, $MnO_2$, $LiCoO_2$, $LiNiO_2$, $LiMnO_2$, CuO, TiS, CuS, FeS, $FeS_2$, copper oxide, copper vanadium oxide, and mixtures thereof.

11. The electrochemical cell of claim 8 wherein the first, third and fifth cathode active materials are $CF_x$ and the second, fourth and sixth cathode active materials are silver vanadium oxide.

12. The electrochemical cell of claim 8 wherein the second and third cathode structures have the configuration: $CF_x$/cathode current collector/silver vanadium oxide.

13. The electrochemical cell of claim 1 wherein the first cathode structure has the configuration: silver vanadium oxide/first cathode current collector/silver vanadium oxide/$CF_x$/silver vanadium oxide/second cathode current collector/silver vanadium oxide.

14. The electrochemical cell of claim 1 wherein the first, second and third cathode current collectors are selected from the group consisting of stainless steel, titanium, tantalum, platinum, gold, aluminum, cobalt nickel alloys, nickel-containing alloys, highly alloyed ferritic stainless steel containing molybdenum and chromium, and nickel-, chromium-, and molybdenum-containing alloys.

15. The electrochemical cell of claim 1 wherein the first, second and third cathode current collectors are titanium having a coating selected from the group consisting of graphite/carbon material, iridium, iridium oxide and platinum provided thereon.

16. The electrochemical cell of claim 1 wherein the first anode structure is of lithium, the first and third cathode active materials are $CF_x$, the second and fourth cathode active materials are silver vanadium oxide and the first, second and third cathode current collectors are titanium.

17. The electrochemical cell of claim 1 wherein the electrolyte has a first solvent selected from an ester, a linear ether, a cyclic ether, a dialkyl carbonate, and mixtures thereof, and a second solvent selected from a cyclic carbonate, a cyclic ester, a cyclic amide, and mixtures thereof.

18. The electrochemical cell of claim 17 wherein the first solvent is selected from the group consisting of tetrahydrofuran, methyl acetate, diglyme, trigylme, tetragylme, dimethyl carbonate, 1,2-dimethoxyethane, 1,2-diethoxyethane, 1-ethoxy, 2-methoxyethane, ethyl methyl carbonate, methyl propyl carbonate, ethyl propyl carbonate, diethyl carbonate, dipropyl carbonate, and mixtures thereof, and the second solvent is selected from the group consisting of propylene carbonate, ethylene carbonate, butylene carbonate, acetonitrile, dimethyl sulfoxide, dimethyl formamide, dimethyl acetamide, γ-valerolactone, γ-butyrolactone, N-methyl-pyrrolidinone, and mixtures thereof.

19. The electrochemical cell of claim 1 wherein the electrolyte includes a lithium salt selected from the group consisting of $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, LiSCN, $LiO_3SCF_3$, $LiC_6F_5SO_3$, $LiO_2CCF_3$, $LiSO_6F$, $LiB(C_6H_5)_4$, $LiCF_3SO_3$, and mixtures thereof.

20. The electrochemical cell of claim 17 wherein the electrolyte is 0.8M to 1.5M $LiAsF_6$ or $LiPF_6$ dissolved in a 50:50 mixture, by volume, of propylene carbonate as the first solvent and 1,2-dimethoxyethane as the second solvent.

21. The electrochemical cell of claim 1 wherein the first anode structure is of lithium and the second cathode structure has the configuration: silver vanadium oxide/third cathode current collector/$Ag_2O$, with the silver vanadium oxide facing the anode.

22. An electrochemical cell, which comprises:
   a) a first cathode structure of a first cathode active material of a first energy density and a first rate capability sandwiched between first and second cathode current collectors, and a second cathode active material of a second energy density and a second rate capability contacted to the first and second cathode current collectors opposite the first cathode active material, wherein the first energy density of the first cathode active material is greater than the second energy density while the first rate capability is less than the second rate capability of the second cathode active material;
   b) a first anode structure of an alkali metal contacted to opposite sides of a first anode current collector, wherein the first anode structure is in electrical association with the second cathode active material contacting the first cathode current collector;
   c) a second cathode structure of a third cathode active material of a third energy density and a third rate capability contacted to one side of a third cathode current collector, and a fourth cathode active material of a fourth energy density and a fourth rate capability contacted to the other side of the third cathode current collector, wherein the third energy density of the third cathode active material is greater than the fourth energy density while the third rate capability is less than the fourth rate capability of the fourth cathode active material and wherein the fourth cathode active material is in electrical association with the first anode structure opposite the second cathode active material contacting the first cathode current collector;

d) a second anode structure of the alkali metal contacted to opposite sides of a second anode current collector, wherein the second anode structure is in electrical association with the second cathode active material contacting the second cathode current collector;

e) a third cathode structure having a fifth cathode active material of a fifth energy density and a fifth rate capability contacted to one side of a fourth cathode current collector, and a sixth cathode active material of a sixth energy density and a sixth rate capability contacted to the other side of the fourth cathode current collector, wherein the fifth energy density of the fifth cathode active material is greater than the sixth energy density while the fifth rate capability is less than the sixth rate capability of the sixth cathode active material and wherein the sixth cathode active material is in electrical association with the second anode structure opposite the second cathode active material contacting the second cathode current collector; and f) a nonaqueous electrolyte activating the first and second anode structures and the first, second and third cathode structures.

23. The electrochemical cell of claim 22 wherein the first, third and fifth cathode active materials are selected from the group consisting of $CF_x$, $Ag_2O$, $Ag_2O_2$, CuF, $Ag_2CrO_4$, $MnO_2$, silver vanadium oxide, and mixtures thereof, wherein $MnO_2$ and silver vanadium oxide are only one of the first, third and fifth cathode active materials when the second and fourth cathode active materials are not $MnO_2$ or silver vanadium oxide and are of a lesser energy density and a greater rate capability than $MnO_2$ or silver vanadium oxide.

24. The electrochemical cell of claim 22 wherein the second, fourth and sixth cathode active materials are selected from the group consisting of silver vanadium oxide, copper silver vanadium oxide, $V_2O_5$, $MnO_2$, $LiCoO_2$, $LiNiO_2$, $LiMnO_2$, CuO, TiS, CuS, FeS, $FeS_2$, copper oxide, copper vanadium oxide, and mixtures thereof.

25. A method for powering an implantable medical device, comprising the steps of:

a) providing the medical device;

b) providing an electrochemical cell, comprising the steps of:

i) providing a first cathode structure of a first cathode active material of a first energy density and a first rate capability sandwiched between first and second cathode current collectors, and a second cathode active material of a second energy density and a second rate capability contacted to the first and second cathode current collectors opposite the first cathode active material, wherein the first energy density of the first cathode active material is greater than the second energy density while the first rate capability is less than the second rate capability of the second cathode active material;

ii) providing a first anode structure of an alkali metal contacted to opposite sides of a first anode current collector, wherein the first anode structure is in electrical association with the second cathode active material contacting the first cathode current collector;

iii) providing a second cathode structure of a third cathode active material of a third energy density and a third rate capability contacted to one side of a third cathode current collector, and providing a fourth cathode active material of a fourth energy density and a fourth rate capability contacted to the other side of the third cathode current collector, wherein the third energy density of the third cathode active material is greater than the fourth energy density while the third rate capability is less than the fourth rate capability of the fourth cathode active material and wherein the fourth cathode active material is in electrical association with the first anode structure opposite the second cathode active material contacting the first cathode current collector; and iv) activating the first anode structure and the first and second cathode structures with a nonaqueous electrolyte; and c) electrically connecting the electrochemical cell to the medical device.

26. The method of claim 25 including selecting the first and third cathode active materials from the group consisting of $CF_x$, $Ag_2O$, $Ag_2O_2$, CuF, $Ag_2CrO_4$, $MnO_2$, silver vanadium oxide, and mixtures thereof, wherein $MnO_2$ and silver vanadium oxide are only one of the first and third cathode active materials when the second and fourth cathode active materials are not $MnO_2$ or silver vanadium oxide and are of are of a lesser energy density and a greater rate capability than $MnO_2$ or silver vanadium oxide.

27. The method of claim 25 including selecting the second and fourth cathode active materials from the group consisting of silver vanadium oxide, copper silver vanadium oxide, $V_2O_5$, $MnO_2$, $LiCoO_2$, $LiNiO_2$, $LiMnO_2$, CuO, TiS, CuS, FeS, $FeS_2$, copper oxide, copper vanadium oxide, and mixtures thereof.

28. The method of claim 25 wherein the first anode structure is of lithium, the first and third cathode active materials are $CF_x$, and the second and fourth cathode active materials are silver vanadium oxide.

29. The method of claim 25 including providing the first cathode structure having the configuration:

silver vanadium oxide/first cathode current collector/$CF_x$/second cathode current collector/silver vanadium oxide.

30. The method of claim 25 including providing the second cathode structure having the configuration:

$CF_x$/third cathode current collector/silver vanadium oxide.

* * * * *